United States Patent
Malisz et al.

(10) Patent No.: US 12,304,891 B2
(45) Date of Patent: *May 20, 2025

(54) REMOVAL OF Al-SALTS, HCl, NaCl AND ORGANIC BY-PRODUCT FROM DIOPAT SUSPENSION BY MEANS OF CERAMIC MEMBRANES IN STRONG ACIDIC CONDITIONS AT HIGH TEMPERATURE

(71) Applicant: BASF SE, Ludwigshafen am Rhein (DE)

(72) Inventors: Jacek Malisz, Ludwigshafen am Rhein (DE); Andreas Mueller, Ludwigshafen am Rhein (DE); Johannes Nagel, Ludwigshafen am Rhein (DE); Dominik Lanzinger, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 1091 days.

This patent is subject to a terminal disclaimer.

(21) Appl. No.: 17/261,865

(22) PCT Filed: Jul. 18, 2019

(86) PCT No.: PCT/EP2019/069390
§ 371 (c)(1),
(2) Date: Jan. 20, 2021

(87) PCT Pub. No.: WO2020/016366
PCT Pub. Date: Jan. 23, 2020

(65) Prior Publication Data
US 2021/0292286 A1 Sep. 23, 2021

(30) Foreign Application Priority Data
Jul. 20, 2018 (EP) ..................................... 18184692

(51) Int. Cl.
| | |
|---|---|
| *C07D 251/24* | (2006.01) |
| *B01D 69/02* | (2006.01) |
| *B01D 71/02* | (2006.01) |
| *C02F 9/00* | (2023.01) |
| *C02F 1/02* | (2023.01) |
| *C02F 1/44* | (2023.01) |
| *C02F 1/66* | (2023.01) |

(52) U.S. Cl.
CPC ........... *C07D 251/24* (2013.01); *B01D 69/02* (2013.01); *B01D 71/025* (2013.01); *C02F 9/00* (2013.01); *B01D 2325/02833* (2022.08); *C02F 1/02* (2013.01); *C02F 1/44* (2013.01); *C02F 1/66* (2013.01)

(58) Field of Classification Search
CPC .................................................. C07D 251/24
See application file for complete search history.

(56) References Cited

U.S. PATENT DOCUMENTS 11,904,279 B2 * 2/2024 Malisz ................. B01D 61/145

FOREIGN PATENT DOCUMENTS

WO 2016/184764 A1 11/2016

OTHER PUBLICATIONS

Angelis, Ceramic membrane filtration of organic compounds: Effect of concentration, pH, and mixtures interactions on fouling, Separation and Purification Technology 118 (2013) 762-775.*
Rakhshan, The effect of functionalized SiO2 nanoparticles on the morphology and triazines separation properties of cellulose acetate membranes, Journal of Industrial and Engineering Chemistry 34 (2016) 51-60.*
Mohammad, Nanofiltration membranes review: Recent advances and future prospects, Desalination, vol. 356, Jan. 15, 2015, pp. 226-254.*
Jiang, "Improved synthesis of 6-( 4-methoxyphenyl )-2, 4-dlchloro-1, 3, 5-triazine and 2,4-bis resorcinyl-substituted UV light absorbing derivatives", Journal of Chemical Rese, vol. 11, Jan. 1, 2008, pp. 664-666.*
International Preliminary Report on Patentability received for PCT Patent Application No. PCT/EP2019/069390, mailed on Feb. 4, 2021, 8 pages.
International Search Report and Written Opinion received for PCT Patent Application No. PCT/EP2019/069390, mailed on Aug. 29, 2019, 12 pages.
Jiang et al., "Improved synthesis of 6-( 4-methoxyphenyl )-2, 4-dlchloro-1, 3, 5-triazine and 2,4-bis resorcinyl-substituted UV light absorbing derivatives", Journal of Chemical Rese, vol. 11, Jan. 1, 2008, pp. 664-666.
Wang et al., "Synthesis, Spectra, and Theoretical Investigations of 1,3,5-Triazines Compounds as Ultraviolet Rays Absorber Based on Time-Dependent Density Functional Calculations and three-Dimensional Quantitative Structure-Property Relationship", Journal of Fluorescence, vol. 28, No. 2, May 2, 2018, pp. 707-723.

* cited by examiner

Primary Examiner — Nizal S Chandrakumar
(74) Attorney, Agent, or Firm — Faegre Drinker Biddle & Reath LLP

(57) ABSTRACT

The present invention provides an improved process for isolating 2,4-bis-(2,4-dihydroxyphenyl)-6-(4-methoxyphenyl)-1,3,5-triazine (DIOPAT) from an aqueous alkaline mixture M comprising the DIOPAT, 2,4-dihydroxybenzophenone, and aluminum salts, wherein the process comprises the steps of precipitating the DIOPAT by acidifying the mixture M to a pH<1; heating the acidified mixture M to a temperature in the range of from 80° C. to 95° C.; and separating of the precipitated DIOPAT from the dissolved 2,4-dihydroxybenzophenone and the dissolved aluminum salts with a ceramic membrane by means of diafiltration.

17 Claims, No Drawings

REMOVAL OF Al-SALTS, HCl, NaCl AND ORGANIC BY-PRODUCT FROM DIOPAT SUSPENSION BY MEANS OF CERAMIC MEMBRANES IN STRONG ACIDIC CONDITIONS AT HIGH TEMPERATURE

CROSS-REFERENCE TO RELATED APPLICATIONS

This application is a national stage application (under 35 U.S.C. § 371) of PCT/EP2019/069390, filed Jul. 18, 2019, which claims benefit of European Application No. 18184692.4, filed Jul. 20, 2018, both of which are incorporated herein by reference in their entirety.

The present invention provides an improved process for isolating 2,4-bis-(2,4-dihydroxyphenyl)-6-(4-methoxyphenyl)-1,3,5-triazine (DIOPAT) from an aqueous alkaline mixture M comprising the 2,4-bis-(2,4-dihydroxyphenyl)-6-(4-methoxyphenyl)-1,3,5-triazine, 2,4-dihydroxybenzophenone, and aluminum salts, wherein the process comprises the steps of precipitating the DIOPAT by acidifying the mixture M to a pH<1; heating the acidified mixture M to a temperature in the range of from 80° C. to 95° C.; and separating of the precipitated DIOPAT from the dissolved 2,4-dihydroxybenzophenone and the dissolved aluminum salts with a ceramic membrane by means of diafiltration.

2,4-bis-(2,4-dihydroxyphenyl)-6-(4-methoxyphenyl)-1,3,5-triazine (DIOPAT) is the staring material for the preparation of the UV absorber Tinosorb® S (also known as 2,2'-[6-(4-methoxyphenyl)-1,3,5-triazine-2,4-diyl] bis{5-[(2-ethylhexyl)oxy]phenol}, anisotriazine, bis-ethylhexyloxyphenol methoxyphenyl triazine, or bemotrizinol; CAS Number 187393-00-6) having the following chemical formula.

Tinosorb® S is a broad band UV absorber, absorbing UVB as well as UVA rays. Thus, Tinosorb® S is an important ingredient for sunscreen compositions and cosmetic applications.

One possible synthesis route to DIOPAT is performed via two steps, starting from 4-bromoanisole and cyanuric chloride under Grignard conditions to form the intermediate DICAT. In the second synthesis step, DICAT is reacted with resorcinol in a Friedel-Crafts reaction to form DIOPAT. In the following, the synthesis route to DIOPAT, starting from 4-bromoanisole and cyanuric chloride, is depicted, wherein the parameters a) Mg, THF, 65° C.; b) cyanuric chloride, THF, 0-5° C.; and c) resorcinol, toluene/benzonitrile, 45° C., $AlCl_3$ are typically applied.

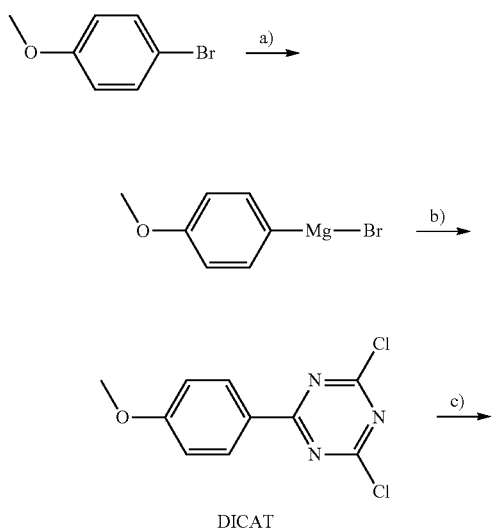

DICAT

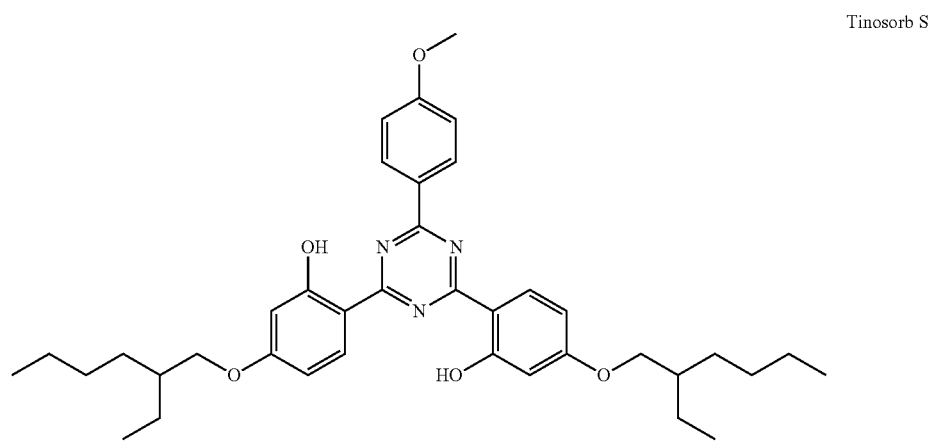 [SMILES: CCCCC(CC)COc1ccc(-c2nc(-c3ccc(OC)cc3)nc(-c3ccc(OCC(CC)CCCC)cc3O)n2)c(O)c1]

Tinosorb S

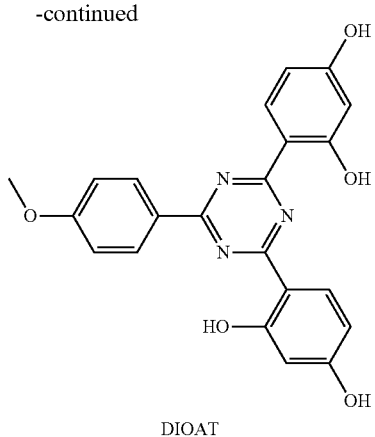

DIOAT

To complete the syntheses to Tinosorb® S, a third step, the alkylation of DIOPAT with isooctyl chloride, is performed. In the following, the reaction to Tinosorb® S is depicted, wherein the parameters a) isooctyl chloride, base, DMF, 143° C. are typically applied.

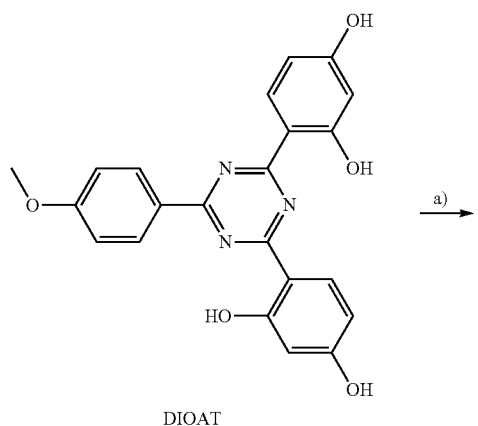

DIOAT

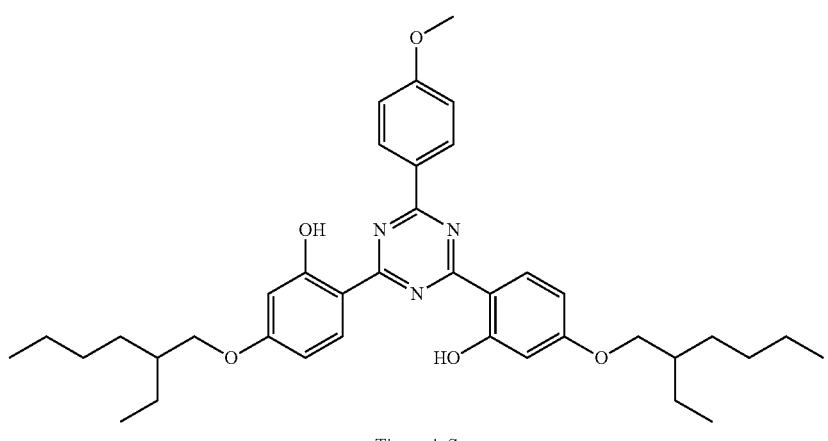

Tinosorb S

In connection with the preparation of DIOPAT, the workup procedure and isolation of DIOPAT causes difficulties.

Typically, the reaction mixture comprising DIOPAT is quenched on a pre-charged sodium hydroxide solution. The product DIOPAT as well as the aluminum salts (Al-salts) from the Friedel-Crafts reaction are then dissolved in the alkaline aqueous sodium hydroxide solution. The organic reaction solvent (e.g. a mixture of toluene and benzonitrile) is separated by phase separation. Residual organic solvents may be stripped off to guarantee an organic solvent free aqueous phase. Then, the DIOPAT is precipitated from the alkaline DIOPAT/Al-salt solution by acidifying the mixture. If a low pH is established (pH<1), the Al-salts are still dissolved in the aqueous phase while the DIOPAT is precipitated as a solid.

However, standard filtration processes, such as the use of a filter press, to separate the precipitated DIOPAT from the Al-salt solution have disadvantages. In particular, the filtration process is a manual, time consuming and open process, which is economically unattractive and causes safety issues on technical scale. Furthermore, the DIOPAT will be obtained together with the undesired organic impurity 2,4-dihydroxybenzophenone (2,4-DHBP), which is a byproduct of the DIOPAT preparation. Impurities of the undesired by-product of 2,4-DHBP in the DIOPAT, which is used for the final reaction step to Tinosorb® S, elevates the consumption of the expensive reactant isooctyl chloride and results in undesired side products, thus increasing the production costs.

An improved separation of the Al-salts from DIOPAT is challenging. Due to the low solubility of DIOPAT in organic solvents that have a complete miscibility gap between the aqueous and the organic phase, a separation of the Al-salts from DIOPAT by phase separation is not suitable. On the other hand, due to the corrosive behavior of acidic AlCl₃/DIOPAT suspensions, most filtration equipment where metallic material is in contact with these suspensions is not suitable. However, the Al-salts, as well as organic by-products, obtained in the Friedel-Crafts reaction with $AlCl_3$ are unfavorable for the following reaction to the final Tinosorb® S and need to be separated from DIOPAT.

Therefore, it was the object of the present invention to provide an improved process for isolating DIOPAT from the DIOPAT/Al-salt solution obtained after quenching the reaction mixture of the Friedel-Crafts reaction for preparing DIOPAT and removing the organic solvents.

It is a further object of the present invention to provide a process for isolating DIOPAT, which avoids a manual, time consuming and open filtration process.

It is another object of the present invention to provide an improved process for isolating DIOPAT, wherein not only aluminum salts but also organic by-products are simultaneously separated from the DIOPAT.

It has surprisingly been found that at least one of these objects can be achieved by a process for isolating 2,4-bis-(2,4-dihydroxyphenyl)-6-(4-methoxyphenyl)-1,3,5-triazine (DIOPAT) from an aqueous alkaline mixture M comprising
  (i) the 2,4-bis-(2,4-dihydroxyphenyl)-6-(4-methoxyphenyl)-1,3,5-triazine;
  (ii) 2,4-dihydroxybenzophenone; and
  (iii) aluminum salts;
wherein the process comprises the steps of
  a) precipitating the 2,4-bis-(2,4-dihydroxyphenyl)-6-(4-methoxyphenyl)-1,3,5-triazine by acidifying the mixture M to a pH<1;
  b) heating the acidified mixture M to a temperature in the range of from 80° C. to 95° C.;
  c) separating the precipitated 2,4-bis-(2,4-dihydroxyphenyl)-6-(4-methoxyphenyl)-1,3,5-triazine from the dissolved 2,4-dihydroxybenzophenone and the dissolved aluminum salts with a ceramic membrane by means of diafiltration with water, whereby the pH increases from <1 to at most 3 and the temperature remains in the range of from 80° C. to 95° C.,
  wherein the separation step c) provides the precipitated 2,4-bis-(2,4-dihydroxyphenyl)-6-(4-methoxyphenyl)-1,3,5-triazine in the form of an aqueous suspension in the retentate, and the dissolved 2,4-dihydroxybenzophenone and the dissolved aluminum salts in the form of an aqueous solution in the permeate.

As indicated above, the main purpose of the process of the present invention is the removal of Al-salts from the mixture M comprising DIOPAT, wherein said mixture is obtained after the Friedel-Crafts reaction, quenching and removal of the organic phase. This object can be achieved by the diafiltration process of the present invention in an advantageous manner, as a closed system can be used, which does not require manual steps. Further, it has been found that also the byproduct 2,4-dihydroxybenzophenone can be separated from the DIOPAT by the diafiltration process of the present invention. In this regard, the high temperature in the range of from 80° C. to 95° C. is advantageous, in order to keep the 2,4-dihydrobenzophenon in solution. Moreover, it has been found that ceramic membranes are particularly advantageous, in order to avoid corrosion issues due to the acidic pH value of the suspension to be separated in the diafiltration process, which is, however, required in order to keep the DIOPAT in precipitated form.

Preferred embodiments of the present invention can be found in the claims, the description and the examples. It is to be understood that the features mentioned above and those still to be illustrated below of the subject matter of the invention are preferred not only in the respective given combination but also in other combinations without leaving the scope of the invention.

Before describing in detail exemplary embodiments of the present invention, definitions important for understanding the present invention are given.

As used in this specification and in the appended claims, the singular forms of "a" and "an" also include the respective plurals unless the context clearly dictates otherwise. In the context of the present invention, the term "about" or "approx." (approximately) denotes an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising".

As used herein, the term "aqueous alkaline mixture M" refers to a mixture comprising components (i), (ii), and (iii) as defined herein, which is typically obtained after quenching the Friedel-Crafts reaction mixture to prepare DIOPAT, i.e. component (i), with an aqueous sodium hydroxide solution and removing the organic phase. The pH of the aqueous alkaline mixture M is preferably in a range of from 10 to 15, more preferably from 12 to 14.

As used herein "2,4-bis-(2,4-dihydroxyphenyl)-6-(4-methoxyphenyl)-1,3,5-triazine" (DIOPAT) is the compound of interest in the process of the present invention, as it is the precursor for the preparation of Tinosorb® S, as explained above. 2,4-dihydroxybenzophenone is a by-product of its preparation. As used herein, the term "aluminum salts" (Al-salts) refers to aluminum salts including aluminum trichloride and/or aluminum hydroxide. These aluminum salts are obtained in the preparation of DIOPAT as aluminum trichloride is required for the Friedel-Crafts reaction.

It is to be understood that the aqueous alkaline mixture M may also comprise further components, e.g. sodium chloride, as a result of the reaction of aluminum trichloride with sodium hydroxide, as well as sodium hydroxide. In addition, sodium aluminum oxide ($NaAlO_2$) may be formed and therefore be present in the aqueous alkaline mixture M. Furthermore, residual amounts of the starting materials DICAT and resorcinol may be present, if the conversion to DIOPAT was incomplete or an excess of DICAT or resorcinol was used.

As used herein, the term "acidified mixture M" refers to a mixture comprising components (i), (ii), and (iii) as defined herein, which is obtained from the aqueous alkaline mixture M after acidification. The acidified mixture M additionally comprises certain amounts of a salt, preferably sodium chloride, from the neutralization reaction. Preferred amounts of the salt obtained due to the neutralization reaction are in the range of from 5% to 15% by weight, based on the total weight of the acidified mixture M. Furthermore, instead of a base, such as sodium hydroxide, an acid will be present, preferably hydrogen chloride. The pH of the acidified mixture M is preferably <1.

As used herein, the term "acidifying" refers to the addition of an acid. Preferred acids include strong inorganic acids, such as sulfuric acid or hydrochloric acid. Preferably, "acidifying" in step a) of the process of the invention is performed with hydrochloric acid, in particular an aqueous hydrogen chloride solution. Preferred concentrations of the hydrogen chloride solution are in the range of from 20 to 37%, preferably in the range of from 36 to 37%. As a result of the acidifying step a), sodium chloride may be formed by reaction of sodium hydroxide with hydrogen chloride.

As used herein, the term "pH<1" refers to a pH of below 1.

As used herein, the term "precipitating" refers to solids formation of a compound. According to the present invention, DIOPAT is precipitated from the mixture M by acidifying the mixture M to a pH<1, whereby the solubility of DIOPAT is significantly reduced, so that a suspension is formed.

As used herein, the term "diafiltration" (DF) refers to a process, wherein a suspension comprising a precipitated compound is separated from dissolved components, which are permeable through a membrane in view of their size. The suspension, which does not pass the membrane is referred to as the "retentate", and the solution comprising the dissolved components, which passes the membrane is referred to as the "permeate". During the diafiltration, the suspension is preferably continuously pumped from the feed vessel to the membrane and from their back to the feed vessel. Typically, diafiltration is performed as a continuous process, wherein additional solvent is continuously added to the retentate, and the permeate is continuously removed. This results in washing of the precipitated compound in the retentate. Preferably, the diafiltration step c) includes washing with water with a washing factor of 3 to 6, preferably 4 to 5, more preferably 4.5, wherein the term "washing factor", also known as "diafiltration factor", refers to the amount of water, also called diafiltration solvent, relative to the suspension as used in step c).

As used herein, the expression that "the pH increases from <1 to at most 3" in the context of step c) of the process of the invention means that the pH may increase during the diafiltration step due to removal of HCl or other acids with additional solvent, in the present case preferably water. The amount of additional solvent will be selected accordingly. For example, a washing factor of 4.5 results in a pH in the range of from 2 to 3, preferably 2.3 to 2.8. Due to the acidic pH value, dissolution of the precipitated DIOPAT and thereby a decrease of the amount of isolated DIOPAT can be avoided. Of course, it is to be understood that the pH does not necessarily increase to a value as indicated above. The pH may also increase less significantly, if less diafiltration solvent is used. Further, as additional solvent is added in a continuous process over time, the pH value will only increase slowly with increasing amount of diafiltration solvent.

As used herein, the expression that "the temperature remains in the range of from 80° C. to 95° C." in the context of step c) of the process of the invention means that the temperature of mixture subjected to the diafiltration step, in particular the temperature of the retentate is kept at a temperature of from 80° C. to 95° C., e.g., by using a heating device or by adding pre-heated washing water. It is important that the temperature remains in this high range, in order to keep 2,4-dihydroxybenzophenone in solution, so that this byproduct can additionally be removed by the diafiltration step. It is to be understood that the temperature may vary within the range of 80° C. to 95° C., when step c) of the process is performed. Preferably, the temperature is at the beginning of the diafiltration of step c) in a range of from 85° C. to 95° C., and then the temperature decreases to a range of from 80° C. to 90° C. over time, e.g. due to the dilution with additional solvent provided at a temperature in the range of from 80° C. to 90° C. Thus, the temperature may be in a range of from 80° C. to 90° C., when the diafiltration step has been carried out under continuous addition of additional solvent.

As used herein, the term "concentration factor" refers to the ratio of the starting volume of the suspension comprising the precipitated compound and the dissolved components to the final volume of the suspension comprising the precipitated compound (retentate), after the dissolved components and parts of the solvent (permeate) have been removed during the diafiltration process. It is to be understood that the concentration factor of the additional solvent, which may be continuously added to the retentate, does not affect the concentration factor, as the same amount of additional solvent, which is continuously added to the retentate, will be continuously removed from the system by removing the permeate.

As used herein, the term "suspension" denotes a heterogeneous mixture comprising a solvent and a precipitate. For the diafiltration process, the particles of the precipitate must be larger than the pore size of the membrane.

As used herein, the term "dissolution" denotes a homogeneous mixture comprising a solvent and dissolved components, for example ions of a salt. In the diafiltration process, the dissolved components must be sufficiently small that they can pass the membrane.

As used herein, the term "feed DIOPAT suspension" refers to the suspension comprising DIOPAT obtained after steps a) and b) of the process according to the present invention.

As used herein, the term "cycle time" refers to the period of time required to complete one cycle of a process for isolating DIOPAT according to the present invention, comprising step a), step b), step c), optionally step d), optionally step e), and optionally step f).

Preferred embodiments regarding the process of the invention are described hereinafter.

As already indicated above, the present invention relates to a process for isolating 2,4-bis-(2,4-dihydroxyphenyl)-6-(4-methoxyphenyl)-1,3,5-triazine (DIOPAT) from an aqueous alkaline mixture M comprising the 2,4-bis-(2,4-dihydroxyphenyl)-6-(4-methoxyphenyl)-1,3,5-triazine, 2,4-dihydroxybenzophenone, and aluminum salts, wherein the process comprises the steps of precipitating the DIOPAT by acidifying the mixture M to a pH<1; heating the acidified mixture M to a temperature in the range of from 80° C. to 95° C.; and separating of the precipitated DIOPAT from the dissolved 2,4-dihydroxybenzophenone and the dissolved aluminum salts with a ceramic membrane by means of diafiltration, whereby the pH increases from <1 to at most 3 and the temperature remains in the range of from 80° C. to 95° C.

In step a) of the process according to the present invention, the acidifying to a pH below 1 may be performed by any suitable organic or inorganic acid. Preferred are inorganic acids, such as hydrogen chloride, hydrogen bromide, hydrogen iodine, sulfuric acid, or nitric acid. In particular, hydrogen chloride is used. Preferably, the acid is in form of an aqueous solution.

Step a) may be performed by addition of the mixture M to an acid, preferably an acidic solution, or by addition of an acid, preferably an acidic solution, to the mixture M. Preferably, step a) is performed by addition of the mixture M to an acidic aqueous solution or by addition of an acidic aqueous solution to the mixture M.

In one embodiment, the invention relates to the process for isolating DIOPAT according to the present invention, wherein acidifying in step a) is performed with hydrogen chloride, preferably by adding the mixture M to an aqueous hydrogen chloride solution.

The low pH value is required to keep the DIOPAT in precipitated form and Al in dissolved form. Thus, a DIOPAT suspension is obtained as acidified mixture M after step a), which comprises DIOPAT in precipitated form, and additionally comprises the 2,4-dihydroxybenzophenone (2,4-DHBP) and aluminum salts. Furthermore, the suspension comprises sodium chloride as neutralization product, if the alkaline aqueous mixture M contained sodium hydroxide and if hydrogen chloride was used for acidifying the mixture M. Typical sodium hydroxide concentrations are in the range of from 5 to 15% by weight based on the total weight of acidified mixture M.

In step b) of the process according to the present invention, the acidified mixture M obtained in step a) is heated to a temperature in the range of from 80° C. to 95° C. This may be done by a suitable heating device. Preferably, the acidified mixture M is heated to a temperature in the range of from 85° C. to 95° C., more preferably from 88° C. to 93° C., in particular to about 90° C.

The high temperatures are advantageous to provide the 2,4-DHBP in dissolved form.

The separation step c) is therefore performed at high temperatures and a low pH value. This limits the possible materials to be used for the diafiltration. In particular, due to the elevated temperature of from 80° C. to 95° C., the high NaCl load of from 5% to 15% by weight, and the acidic conditions (pH<1) of the DIOPAT suspension, the DIOPAT suspension is very corrosive to steel.

According to the present invention, any suitable ceramic membrane may be applied. Thereby, a suitable ceramic membrane needs to fulfill at least the criteria that i) no corrosion will take place, ii) the membrane is permeable for the dissolved components, in particular for sodium chloride, aluminum trichloride and also for the organic by-products, such as 2,4-DHBP, iii) the membrane is resistant to a pH below 1, and iv) the membrane is suitable for applications at temperatures of from 80 to 95° C.

Suitable ceramic membrane materials are selected from the group consisting of $TiO_2$, $ZrO_2$, or $Al_2O_3$. The most preferred ceramic membrane material is $Al_2O_3$.

In one embodiment, the invention therefore relates to the process for isolating DIOPAT according to the present invention, wherein the ceramic membrane is a $TiO_2$, $ZrO_2$, or $Al_2O_3$ membrane, preferably an $\alpha$-$Al_2O_3$ membrane.

The ceramic membrane according to the present invention may have a pore size in the range of from 10 to 800 nm, preferably from 20 to 500 nm, more preferably from 30 to 400 nm, even more preferably from 40 to 200 nm, and especially preferably from 50 to 100 nm. Preferably, the pore size of the ceramic membrane is provided as the mean pore size as determined by the bubble-test described in American Society for Testing and Materials Standard (ASMT) Method F316. Alternatively, the pore size of the ceramic membranes may be defined by the molecular weight cut off, which is preferably in the range of from 1 kD to 150 kD.

In a preferred embodiment of the process of the invention, the ceramic membrane has a pore size in the range of from 20 to 500 nm, preferably from 50 to 100 nm.

The ceramic membrane may be provided in the form of a tubular, multi-channel or monolithic element, wherein a multi-channel element is preferred. Typically, the ceramic material has a multilayer structure with pore sizes ranging from larger pore sizes to smaller pore sizes, in order to provide, e.g. a macroporous support and a microporous top layer oriented to the retentate.

For example, a ceramic membrane having a pore size of 50 nm as the relevant value for the diafiltration step may comprise membrane layers with pore sizes of 400 nm, 200 nm, and 50 nm, wherein the smaller pore sizes will be on the side of the retentate. For the characterization of the ceramic membrane regarding the filtration properties, the smallest pore size oriented to the permeate is of relevance.

In a preferred embodiment, the ceramic membrane is an $\alpha$-$Al_2O_3$ membrane having a pore size of 50 nm with 400/200/50 nm membrane layers.

In one embodiment of the present invention, the ceramic membrane is a tubular ceramic membrane, through which the retentate flows, while the permeate stream exits the tubular ceramic membrane laterally through the ceramic membrane.

In another embodiment of the present invention, the ceramic membrane is a multi-channel element comprising several channels within the ceramic membrane material, e.g. from 7 to 211 channels, preferably from 7 to 37 channels, wherein the retentate flows through the channels, while the permeate stream exits the multi-channel element laterally through the ceramic membrane. In a particular embodiment of the present invention, suitable multi-channel elements comprise 7, 19, 37, 61, 85, or 211 channels, preferably 7 or 19 channels.

The length of the multi-channel element is preferably in a range of from 0.5 to 2 m, preferably from 0.5 to 1.5 m, more preferably from 1.0 to 1.5 m.

The inner diameter of the channels of the multi-channel element is preferably in the range of from 2 to 8 mm. The overall diameter of the multi-channel element is preferably in the range of from 25 to 80 mm, preferably from 25 to 41 mm, more preferably 25.4 or 41 mm.

Thus, in a preferred embodiment of the invention, the ceramic membrane is provided in the form of a multi-channel element having a length of from 0.5 to 1.5 m and an inner channel diameter of from 3 to 8 mm, preferably of 6 mm, wherein the multi-channel element preferably comprises from 7 to 19 channels. Particularly preferred is a multi-channel element having a length of from 1.0 to 1.5 m, an inner channel diameter of 6 mm, wherein the multi-channel element preferably comprises 7 or 19 channels. The overall diameter is then preferably from 25 or 41 mm.

The filter surface per element can be calculated from the length, the inner channel diameter and the number of channels of the element. In certain embodiments, the filter surface per element is from 0.02 to 3 $m^2$, preferably from 0.02 to 2 $m^2$, more preferably from 0.05 to 1.5 $m^2$, in particular from 0.1 to 0.6 $m^2$.

According to the invention, a single-channel element may have, e.g., a 1/6 or a 1/16 geometry. Thereby, the 1/6 geometry denotes that the element has one channel and an inner channel diameter of 6 mm. A 1/16 geometry thus denotes that the element has one channel and an inner diameter of 16 mm.

According to the invention, the multi-channel element may have, e.g., a 7/6 (i.e. the element has seven channels and an inner channel diameter of 6 mm), a 19/3.3, a 37/2, a 19/4, a 19/6, a 37/3.8, a 61/2.5, a 19/8, a 85/3.3, or a 211/2 geometry. In one preferred embodiment, the multi-channel element has a 7/6 or 19/6 geometry and 1.2 to 1.5 m length. Particularly preferred is a multi-channel element with a 19/6 geometry and 1.5 m length.

In one embodiment, the diafiltration step of the process according to the invention is performed at a feed pressure of from 0.5 to 5 bar, preferably from 1.0 to 3.5 bar, and more preferably from 1.5 to 3.0 bar. In this connection, the term "feed pressure" refers to the pressure with which the feed DIOPAT suspension, i.e. the heated acidified mixture M obtained in step b) is provided to perform the diafiltration step, i.e. the pressure with which feed DIOPAT suspension is passed through the ceramic membrane element, in order to separate the precipitated DIOPAT from the dissolved 2,4-DHBP and the dissolved aluminum salts by means of diafiltration.

In one embodiment, the diafiltration step of the process according to the invention is performed at a cross flow of from 1.5 to 5 m/s, preferably from 2 to 5 m/s, more preferably from 2.5 to 4 m/s, and in particular from 3 to 4 m/s.

In one embodiment, the invention relates to the process for isolating DIOPAT according to the present invention, wherein, in the diafiltration step, the feed pressure is from 1.0 to 3.5 bar and the cross flow is from 2 to 5 m/s.

The purity of the DIOPAT obtained in step c) of the process of the invention may be increased by washing the suspension in the retentate of the diafiltration step with water. Preferably, washing water is continuously introduced into the diafiltration system on the retentate side, while the permeate is continuously removed. Due to the dilution with water, the pH value in the retentate may increase over time. However, the amount of water is adapted such that the pH value increases to a value of at most 3, preferably at most 2.5. Furthermore, it is required to preheat the washing water, in order to ensure that the temperature remains in the range of from 80° C. to 95° C., although a slight decrease within this range over time is acceptable, so that the temperature in step c) may drop to from 80° C. to 90° C. after, e.g., 1 hour.

In a preferred embodiment, the separation step c) therefore involves continuous washing of the suspension in the retentate with water, and removing of the permeate, whereby the pH slowly increases from <1 to at most 3 and the temperature remains in the range of from 80 to 95° C. Preferably, the overall volume of the retentate and the permeate is kept constant by removing the same volume of permeate as the volume of washing water that is introduced into the retentate.

During the washing process, the DIOPAT concentration remains constant. To separate the Al-salts and organic by-products, the DIOPAT suspension is pumped from the feed vessel to the ceramic membrane element and from there back to the feed vessel. In the ceramic membrane, the dissolved components (Al-salts and some organic components such as 2,4-DHBP) pass through the membrane. The DIOPAT particles stay in the suspension and go back to the feed vessel. The aqueous phase with the dissolved components (e.g. Al-salts and organic components such as 2,4-DHBP) passing through the membrane is called permeate, the suspension, comprising DIOPAT, that goes back to the feed vessel is called retentate. The permeate is preferably sent to a waste water treatment plant. Thus, the process may preferably be performed as a batch process. Alternatively, the process may be performed as a continuous process. This would require that the ultrafiltration unit comprises 3 or 4 filtration loops, which are connected in series. The diafiltration water then has to be added to each filtration loop.

The feed DIOPAT suspension may be washed with a washing factor of e.g. 2, meaning that the amount of water used for washing the DIOPAT suspension is equal to 2 times of the DIOPAT suspension amount. The higher the washing factor, the lower will be the Al-salt concentration in the retentate and the lower will be the 2,4-DHBP concentration.

It is preferred to wash with a washing factor of 3, more preferably with a washing factor of 4 or 5.

In one preferred embodiment, the amount of washing water is at least three times as high as the amount of the suspension in the retentate. In another preferred embodiment, the amount of washing water is at most six times as high as the amount of the suspension in the retentate.

To keep the temperature of the retentate at from 80° C. to 95° C. during the whole washing process, it may be preferred to preheat the washing water by an external heat exchanger. Alternatively, the washing water may be heated before use by direct steam injection.

Accordingly, in one embodiment, the washing water is heated before use, preferably by an external heat exchanger or direct steam injection.

The diafiltration step c) also results in concentrating the feed DIOPAT suspension to a certain extent, as the permeate is separated. The volume of the retentate is then kept constant during the washing with water as indicated above. The concentration factor defines the ratio of the volume of the feed DIOPAT suspension to the volume of the retentate comprising the precipitated DIOPAT.

In one embodiment, the concentration factor of the retentate is less than 2.5, preferably less than 1.9, more preferably less than 1.8. In another embodiment, the concentration factor of the retentate is in a range of from 1.4 to 2, preferably from 1.5 to 1.9, more preferably from 1.6 to 1.8.

In one embodiment, the concentration factor of the retentate is less than 2.5, preferably from 1.6 to 1.8.

In one embodiment, the total diafiltration factor, also referred to as washing factor, as defined above, is less than 6, preferably less than 5. In another embodiment, the total diafiltration factor is in the range of from 2 to 7, preferably from 3 to 6, in particular from 3.5 to 5.5, e.g. 4.5.

In summary, the process of the present invention comprising steps a), b), and c) provides the DIOPAT in precipitated form in the form of an aqueous suspension in the retentate of the diafiltration. The obtained aqueous suspension of DIOPAT is concentrated in comparison to the alkaline mixture M. Furthermore, 2,4-DIOPAT and aluminum salts as well as additional salts, which are, e.g., formed during acidifying the mixture M have been separated as the permeate from the aqueous DIOPAT suspension.

In one embodiment, the amount of Al-salts in the DIOPAT suspension after step c) is less than about 0.02 wt.-%, preferably less than about 0.015 wt.-%, more preferably less than about 0.01 wt.-%, in particular less than about 0.008 wt.-%, based on the total weight of the DIOPAT suspension after step c).

In one embodiment, the amount of 2,4-DHBP in the DIOPAT suspension after step c) is less than about 0.3 wt.-%, preferably less than about 0.2 wt.-%, more preferably less than about 0.15 wt.-%, in particular less than about 0.1 wt.-%, based on the total weight of the DIOPAT suspension after step c).

In one embodiment, the amount of DIOPAT in the DIOPAT suspension after step c) is at least about 1.5 wt.-%, preferably at least about 2 wt.-%, more preferably at least about 3 wt.-%, in particular at least about 4 wt.-%, based on the total weight of the DIOPAT suspension after step c).

In another embodiment, the amount of resorcinol in the DIOPAT suspension is reduced by at least about 80%, preferably at least about 85%, more preferably at least about 90%, after step c), compared to the amount of resorcinol in the feed DIOPAT suspension.

In one embodiment, the amount of benzoic acid in the DIOPAT suspension is reduced by at least about 80%, preferably at least about 90%, more preferably at least about 95%, after step c), compared to the amount of benzoic acid in the feed DIOPAT suspension.

In one embodiment, the amount of 2,4-DHBP in the DIOPAT suspension is reduced by at least about 60%, preferably at least about 70%, more preferably at least about 80%, after step c), compared to the amount of 2,4-DHBP in the feed DIOPAT suspension.

In one embodiment, the amount of Al-salts in the DIOPAT suspension is reduced by at least about 80%, preferably at least about 90%, more preferably at least about 95%, after step c), compared to the amount of Al-salts in the feed DIOPAT suspension.

In one embodiment, the amount of NaCl in the DIOPAT suspension is reduced by at least about 80%, preferably at least about 90%, more preferably at least about 95%, after step c), compared to the amount of NaCl in the feed DIOPAT suspension.

The process of the invention may further comprise neutralizing and concentrating the obtained aqueous suspension comprising DIOPAT of the retentate. It is to be understood that this step may also be part of step c).

In one embodiment, the process according to the present invention further comprises the step of neutralizing the aqueous suspension of the retentate. Thereby, the suspension preferably is neutralized to obtain a pH of from 5 to 9, more preferably from 6 to 8, in particular about 7.

Directly after the neutralization of step d), the DIOPAT suspension has a solid content in the range of from about 1% to about 10%, preferably from about 2% to about 8%, more preferably from about 3% to about 6%, in particular from about 5% to about 6%, in each case based on the total weight of the DIOPAT suspension.

Optionally, the aqueous suspension of the retentate may simultaneously be concentrated while neutralizing, preferably neutralizing the aqueous suspension of the retentate to obtain a pH of from 5 to 9, more preferably from 6 to 8, in particular about 7. Alternatively, the aqueous suspension of the retentate may be concentrated after neutralizing, preferably neutralizing the aqueous suspension of the retentate to obtain a pH of from 5 to 9, more preferably from 6 to 8, in particular about 7.

Neutralizing in step d) may be performed by any suitable base known in the art. The base may be an inorganic or an organic base, preferably an inorganic base, more preferably sodium hydroxide or sodium carbonate, in particular sodium hydroxide.

In one embodiment, the invention relates to the process for isolating DIOPAT according to the present invention, wherein the process further comprises the step of d) neutralizing the aqueous suspension of the retentate obtained in step c) to obtain a pH of from 6 to 8, and optionally simultaneously concentrating the aqueous suspension.

In one embodiment, the invention relates to the process for isolating DIOPAT according to the present invention, wherein neutralizing in step d) is performed with sodium hydroxide or sodium carbonate, preferably with sodium hydroxide.

In one embodiment, the process according to the present invention further comprises the concentrating step e) of the aqueous suspension obtained in step d), which is also referred to as a de-watering process. Concentrating may be performed by any method known in the art such as evaporation or filtration, preferably filtration. With regard to concentrating by filtration, any known filter may be used, such as a Dyno Filter (Bokela).

The concentration step e) may be performed after washing the neutralized aqueous suspension with water. Alternatively, the concentration step e) may be performed without prior washing the neutralized aqueous suspension with water. In one preferred embodiment, the concentration step e) is performed after washing the neutralized aqueous suspension with water.

Generally, the concentrating results in an increase of the solid content in the aqueous suspension from about 2% to about 8% up to about 10% to about 25%, preferably from about 3% to about 6% up to about 12% to about 20%, more preferably from about 4% to about 5% up to about 15% to about 16%, in each case based on the total weight of the DIOPAT suspension.

In one embodiment, the invention relates to the process for isolating DIOPAT according to the present invention, wherein the process further comprises the step of e) concentrating the neutralized aqueous suspension by filtration, after optionally washing the neutralized aqueous suspension with water.

In one embodiment, the invention relates to the process for isolating DIOPAT according to the present invention, wherein the process further comprises the step of f) drying the concentrate obtained in step e).

Drying may be performed by any method known in the art such as spray drying, evaporation, air drying, under vacuum, filtration, centrifugation, freeze drying, or mixtures thereof, preferably spray drying. Suitable spray drier are jet or disc spray drier.

In one embodiment, the amount of Al-salts in the dried DIOPAT mass is less than about 0.5 wt.-%, preferably less than about 0.4 wt.-%, more preferably less than about 0.3 wt.-%, in particular less than about 0.2 wt.-%, based on the total weight of the dried DIOPAT mass.

In one embodiment, the amount of 2,4-DHBP in the dried DIOPAT mass is less than about 5 wt.-%, preferably less than about 3 wt.-%, more preferably less than about 2 wt.-%, in particular less than about 1.8 wt.-%, based on the total weight of the dried DIOPAT mass.

In one embodiment, the amount of DIOPAT in the dried DIOPAT mass is at least about 80 wt.-%, preferably at least about 83 wt.-%, more preferably at least about 85 wt.-%, in particular at least about 87 wt.-%, based on the total weight of the dried DIOPAT mass.

In a particular embodiment, the invention relates to the process for isolating DIOPAT according to the present invention, wherein the separation step c) involves continuous washing of the suspension in the retentate with water, and removing of the permeate, and wherein the process further comprises the steps of
d) neutralizing the aqueous suspension of the retentate obtained in step c) to obtain a pH of from 6 to 8, and optionally simultaneously concentrating the aqueous suspension;
e) concentrating the neutralized aqueous suspension obtained in step d) by filtration, optionally after washing the neutralized aqueous suspension with water; and
f) drying the concentrate obtained in step e).

The process for isolation DIOPAT according to the present invention is especially advantageous in view of production costs, as due to unexpected removal of 2,4-DHBP from the DIOPAT suspension, the consumption of the expensive reactant isooctyl chloride in the last reaction step to Tinosorb® S is reduced significantly. This reduces the costs of the final synthesis step to Tinosorb® S as well as the costs of product workup of Tinosorb® S to reach the final specification.

The diafiltration process according to the present invention further provides a much more stable and higher performance of the diafiltration, thereby producing similar quality results as in the previously performed process using the FP.

Further, the diafiltration process according to the present invention provides a process for isolating DIOPAT, involving less manual process steps, which is therefore also more hygienic.

The present invention is further illustrated by the following example.

EXAMPLE

Diafiltration (DF) experiments were conducted in a low-pressure lab unit, designed for operation with HCl solutions up to 90° C.

The feed reactor was replaced by a long tube with heating jacket without agitator. This allowed homogeneous movement of the suspension with diafiltration (DF) water into the feed pump which made the final homogenization. Additionally, to avoid negative effects from clumps in suspension, the suspension was homogenized by means of an ultra-speed agitator (Ultra Turrax®).

Membrane Used:
  Channel element 6 mm channel, 1 m long
  Membrane material α-$Al_2O_3$
  Nominal pore size 50 nm with 400/200/50 membrane layers Operating Parameters:
  Temperature 85-90° C.
  Cross flow 3.5 and 4 m/s
  Feed pressure 1.5-2.5 bars Process Parameters:
  Dilution factor of the start suspension only dead volume of the pump
  Total concentration factor (CF) up to 2
  Total diafiltration factor 4.5
  Sampling: The sampling and the analysis were the same independent from the process step. After each total diafiltration factor or CF step, samples of permeate and retentate were taken for:
  Dry content (DC) and NaCl content
  Al content
  Total Organic Carbon (TOC, only permeates)
  DIOPAT content and content of side products (AHRT, 2,4-DHBP, DMPRT)
  DC was measured with DC scales, NaCl was measured by titration, TOC was measured with a TOC analyzer. DIOPAT and side products were determined via HPLC using
  Agilent 1100
  column material: EUROSPH ER 100-C18/5 Knauer
  column length: 25 cm, column diameter: 4 mm
  column temperature: 20° C.
  injection volume: 5 μl
  mobile phase: eluent A: 900 Deionat (2)+100 acetate buffer pH 4.65 (3)+0.2% TBAHS, eluent B: acetonitrile (1)+0.2% TBAHS
  method: flow: 1.0 mL/min, pressure: max. 400 bar, stop time: 30 min timetable:

| Time | % A | % B |
|---|---|---|
| 5 min | 50% | 50% |
| 25 min | 0% | 100% |
| 30 min | 0% | 100% |

According to the present invention, the Al-salts as well as undesired organic by-products are separated with a ceramic membrane by means of diafiltration with water. The cycle time was around 1 hour. Therefore, 3 kg DIOPAT suspension, comprising 93.2 g DIOPAT, 1.8 g resorcinol, 6.0 g benzoic acid, 2.4 g anisyl-hydroxy-resorcinyl-triazine (AHRT), 9.6 g 2,4-DHBP, 1.8 g DMPRT (dimethoxyphenylresorcinyltriazine), 2.544 kg water, 330.0 g NaCl, and 11.1 g $AlCl_3$, was transferred to a vessel of suitable size.

The temperature was adjusted to 90° C. The 2,4-DHBP concentration in the feed DIOPAT suspension of the diafiltration was about 0.32%. The solubility of 2,4-DHBP in acidic water at 90° C. was about 0.18%. Thus, some 2,4-DHBP probably was already precipitated and had to be brought back into solution during the DF process. In the DF process, the DIOPAT suspension was held at 90° C. and was permanently washed with 12 kg fresh water. During the washing process, the DIOPAT concentration stayed constant. To separate the Al-salts and organic by-products, the DIOPAT suspension was pumped from the feed vessel to a ceramic membrane module and from there back to the feed vessel. In the ceramic membrane, the dissolved components (Al-salts and some org. components such as 2,4-DHBP) passed through the membrane. The DIOPAT particles stayed in the suspension and went back to the feed vessel. The permeate was send to the waste water treatment plant. In total, the suspension at the beginning of the membrane process (suspension after precipitation) was washed with a washing factor of 4.5. Then, the Al-salt concentration in the retentate was less than approx. 65 ppm.

The aqueous suspension was neutralized by 1.3 g NaOH (50% w/v). The neutralized retentate was concentrated by means of a Dyno Filter from Bokela to obtain 685.8 g of DIOPAT suspension, comprising 96.0 g (14%) DIOPAT.

After spray drying, 106.9 g spray dried DIOPAT mass, comprising 96.0 g (87.2%) DIOPAT, 0.07 g (0.05%) resorcinol, 0.10 g (0.1%) benzoic acid, 2.2 g (2.1%) AHRT, 1.7 g (1.6%) 2,4-DHBP, 1.8 g (1.7%) DMPRT (dimethoxyphenylresorcinyltriazine), 3.2 g (3%) water, 4.5 g (4.2%) NaCl, and 0.14 g (0.13%) $AlCl_3$, was obtained.

Comparison of the effect of the temperature on the removal of 2,4-DHBP:

To assess the influence of the temperature on the residual amounts of 2,4-DHBP in the obtained DIOPAT concentrate after ultrafiltration, the procedure as described above was repeated under the following temperature conditions:

| | UF1 (72° C.) | | UF2 (89° C.) | |
|---|---|---|---|---|
| Parameter | Susp [%] | Concentrate [%] | Susp [%] | Concentrate [%] |
| NaCl | 14.63 | 0.49 | 14.63 | 0.24 |
| DC | 13.78 | 5.85 | 13.78 | 5.32 |
| Diopat | 3.00 | 4.65 | 3.00 | 4.67 |
| 2,4-DHBP | 0.28 | 0.26 | 0.28 | 0.07 |
| NaCl/Diopat | 487.7 | 10.5 | 487.7 | 5.1 |
| Diopat/DC | 21.8 | 79.5 | 21.8 | 87.8 |
| 2,4-DHBP/Diopat | 9.3 | 5.6 | 9.3 | 1.5 |

As can be seen, the amount of 2,4-DHBP in the Concentrate is significantly reduced, if the ultrafiltration is performed at temperatures of 88-91° C. in comparison to temperatures of 71-76° C.

The invention claimed is:

1. A process for isolating 2,4-bis-(2,4-dihydroxyphenyl)-6-(4-methoxyphenyl)-1,3,5-triazine (DIOPAT) from an aqueous alkaline mixture M comprising
   (i) the 2,4-bis-(2,4-dihydroxyphenyl)-6-(4-methoxyphenyl)-1,3,5-triazine;
   (ii) 2,4-dihydroxybenzophenone; and
   (iii) aluminum salts;
   wherein the process comprises the steps of
   a) precipitating the 2,4-bis-(2,4-dihydroxyphenyl)-6-(4-methoxyphenyl)-1,3,5-triazine by acidifying the mixture M to a pH<1;
   b) heating the acidified mixture M to a temperature in the range of from 80° C. to 95° C.;
   c) separating the precipitated 2,4-bis-(2,4-dihydroxyphenyl)-6-(4-methoxyphenyl)-1,3,5-triazine from the dissolved 2,4-dihydroxybenzophenone and the dissolved aluminium salts with a ceramic membrane by means of diafiltration with water, whereby the pH increases from <1 to at most 3 and the temperature remains in the range of from 80° C. to 95° C.,
   wherein the separation step c) provides the precipitated 2,4-bis-(2,4-dihydroxyphenyl)-6-(4-methoxyphenyl)-1,3,5-triazine in the form of an aqueous suspension in the retentate, and the dissolved 2,4-dihydroxybenzophenone and the dissolved aluminum salts in the form of an aqueous solution in the permeate.

2. The process of claim 1, wherein acidifying in step a) is performed with hydrogen chloride, by adding the mixture M to an aqueous hydrogen chloride solution.

3. The process of claim 1, wherein the ceramic membrane is a $TiO_2$, $ZrO_2$, or $Al_2O_3$ membrane.

4. The process of claim 1, wherein the ceramic membrane has a pore size in the range of from 20 to 500 nm.

5. The process of claim 1, wherein the ceramic membrane has a pore size in the range of from 50 to 100 nm.

6. The process of claim 1, wherein the ceramic membrane is an $\alpha$-$Al_2O_3$ membrane having a pore size of 50 nm.

7. The process of claim 1, wherein the ceramic membrane is an $\alpha$-$Al_2O_3$ membrane having a pore size of 50 nm, and with 400/200/50 nm membrane layers.

8. The process of claim 1, wherein the ceramic membrane is provided in the form of a multi-channel element having a length of from 0.5 to 1.5 m and a channel diameter of from 3 to 8 mm, wherein the multi-channel element comprises from 7 to 19 channels.

9. The process of claim 1, wherein the feed pressure is from 1.0 to 4 bar and the cross flow is from 2 to 5 m/s.

10. The process of claim 1, wherein the separation step c) involves continuous washing of the suspension in the retentate with water, and removing of the permeate.

11. The process of claim 10, wherein the amount of washing water is at least three times as high as the amount of the suspension in the retentate.

12. The process of claim 10, wherein the washing water is heated before use, preferably by an external heat exchanger or direct steam injection.

13. The process of claim 1, wherein the concentration factor of the retentate is less than 2.5.

14. The process of claim 1, wherein the process further comprises the step of
   d) neutralizing the aqueous suspension of the retentate obtained in step c) to obtain a pH of from 6 to 8, and optionally simultaneously concentrating the aqueous suspension.

15. The process of claim 14, wherein neutralizing in step d) is performed with sodium hydroxide or sodium carbonate.

16. The process of claim 14, wherein the process further comprises the step of
   e) concentrating the neutralized aqueous suspension obtained in step d) by filtration, optionally after washing the neutralized aqueous suspension with water.

17. The process of claim 16, wherein the process further comprises the step of
   f) drying the concentrate obtained in step e).

* * * * *